United States Patent [19]

Hamsher et al.

[11] 4,113,566

[45] Sep. 12, 1978

[54] PROCESS FOR PREPARING 6-AMINOPENICILLANIC ACID

[75] Inventors: James J. Hamsher, Gales Ferry; Merrill Lozanov, East Lyme, both of Conn.

[73] Assignee: Pfizer Inc., New York, N.Y.

[21] Appl. No.: 745,212

[22] Filed: Nov. 26, 1976

[51] Int. Cl.$^2$ ............................................ C12D 13/06
[52] U.S. Cl. .................................. 195/36 P; 195/115
[58] Field of Search ................ 195/36 P, 31 R, 31 F, 195/115

[56] References Cited

U.S. PATENT DOCUMENTS

| | | | |
|---|---|---|---|
| 3,239,427 | 3/1966 | Huang et al. | 195/36 P |
| 3,694,314 | 9/1972 | Lloyd et al. | 195/31 F |
| 3,910,825 | 10/1975 | Huper et al. | 195/36 P |
| 3,915,797 | 10/1975 | Ishimatsu et al. | 195/31 R |

FOREIGN PATENT DOCUMENTS

1,348,359   3/1974   United Kingdom.

*Primary Examiner*—Alvin E. Tanenholtz
*Attorney, Agent, or Firm*—Connolly and Hutz

[57] ABSTRACT

A simple and efficient process for the deacylation of penicillins to 6-aminopenicillanic acid in which an aqueous penicillin solution is rapidly recirculated through a shallow bed comprising particulate immobilized penicillin acylase at 15°–45° C and pH 6.5–9.0 until substantial conversion results.

5 Claims, No Drawings

PROCESS FOR PREPARING 6-AMINOPENICILLANIC ACID

BACKGROUND OF THE INVENTION

This invention relates to penicillins. More specifically, it relates to the enzymatic deacylation of penicillins to 6-aminopenicillanic acid.

6-Aminopenicillanic acid, commonly referred to as 6-APA, is an intermediate in the manufacture of synthetic penicillins and is prepared among other means by the deacylation of penicillins. This conversion has been effected by both chemical and biochemical techniques. The chemical conversion, as exemplified by U.S. Pat. No. 3,499,909, suffers from being a multi-step process requiring energy-intensive low-temperature conditions and specialized equipment. The biochemical conversion utilizes the enzyme penicillin acylase, or penicillin amidase. In U.S. Pat. No. 3,260,653, the enzyme activity is supplied by certain bacteria or bacterial extracts. This approach is not entirely satisfactory for the industrial production of 6-APA since the product stream is contaminated with the enzyme and/or microbial cells, which must then be removed during product recovery, and the enzyme is used only once. The problems of product contamination and poor enzyme utilization are purportedly overcome in U.S. Pat. No. 3,953,291 by the use of immobilized penicillin amidase-producing microbial cells. Such a process using immobilized cells is still characterized by low productivity, however, since in batch operation the process suffers from its non-continuous nature and excessive handling of the immobilized cell material, while in column operation it suffers from poor pH control and less than optimum enzyme utilization.

The use of a shallow bed of microbial cell catalyst for the continuous isomerization of glucose to fructose is disclosed in U.S. Pat. Nos. 3,694,314 and 3,817,832. The shallow bed is reportedly employed to minimize the pressure drop through the catalyst, the desired conversion being achieved by passing the aqueous process stream through several beds in series.

SUMMARY OF THE INVENTION

It has now been found that penicillins can be converted to 6-APA in a simple and efficient manner by rapidly recirculating an aqueous penicillin solution through a shallow bed comprising particulate penicillin acylase catalyst under controlled temperature and pH conditions. Accordingly, the present invention entails a process for the enzymatic conversion of a penicillin to 6-APA which comprises recirculating an aqueous solution of the penicillin through a bed up to about 6 cm deep comprising particulate immobilized penicillin acylase catalyst at a flow rate of at least 0.4 bed volume per minute while maintaining the solution at a temperature of from about 15° to 45° C and a pH from about 6.5 to 9.0 and continuing the recirculation until the penicillin is substantially converted to 6-APA. Preferably the penicillin is potassium penicillin G, the bed has a depth of from about 2 to 3 cm, the particulate catalyst comprises immobilized *Proteus rettgeri* cells containing the enzyme, the temperature is about 35° to 40° C and the pH is from about 7.5 to 8.2.

DETAILED DESCRIPTION OF THE INVENTION

The process of the present invention, in rapidly recirculating the process stream through a shallow bed of particulate catalyst, is thus able to optimize the conversion of penicillins to 6-APA since it overcomes the heretofore unsolved problems of pH and flow control associated with continuous column deacylation and of excessive catalyst handling with batch deacylations. The capability of the process to control pH is especially significant since the deacylation generates a carboxylic acid which must be neutralized, the enzyme is optimally active over a narrow pH range and both the reactant and product are sensitive to pH extremes. Since this control is accomplished with a minimum of pressure drop through the bed, the process has the further advantage of utilizing standard process equipment.

The process is suitable for the deacylation of any water-soluble penicillin. Representative penicillins include but are not limited to penicillin G (benzylpenicillin), penicillin X (p-hydroxybenzylpenicillin) and penicillin V (phenoxymethylpenicillin). Preferred is penicillin G in the form of the potassium or sodium salt. The concentration of the penicillin substrate in the aqueous solution is not critical and normally varies from about 1 to 20 g/100 ml solution.

By particulate immobilized penicillin acylase catalyst is meant the enzyme penicillin acylase, or any penicillin acylase-producing microorganism, entrapped within or attached to or on a water-insoluble particulate matrix of organic or inorganic origin in such a manner as to retain the enzyme's activity. Suitable penicillin acylase-producing microorganisms include those belonging to the general of Proteus, Escherichia, Streptomyces, Nocardia, Micrococcus, Pseudomonas, Alkaligenes and Aerobacter such as disclosed in U.S. Pats. Nos. 3,260,653 and 3,953,291. The common methods employed for such immobilization of enzymes and microbial cells include covalent bonding to the matrix, entrapment within the matrix, physical adsorption on the matrix and crosslinking with a bifunctional reagent to form the matrix. Illustrative of these immobilization techniques are those of U.S. Pats. Nos. 3,645,852, 3,708,397, 3,736,231, 3,779,869, 3,925,157, 3,953,291 and 3,957,580. As indicated by these references, the matrix is typically a polymer or copolymer of such monomers as glycidyl methacrylate methacrylic acid anhydride, acryloylamide, acrylamide, styrene, divinylbenzene or glucose, or the matrix may be of such substances as bentonite, powdered carbon, titania, alumina or glass. Preferred catalyst is one in which *Proteus rettgeri* cells containing penicillin acylase are immobilized by the process of U.S. Pat. No. 3,957,580. Such particulate catalysts will normally have an activity of from about 200 to 5,000 units (micromoles penicillin G deacylated per hour) per gram of dry catalyst.

The particulate catalyst is utilized in the form of a shallow bed through which the process stream is rapidly recirculated. By shallow bed is meant a bed having a depth of up to about 6 cm. The actual depth of the bed is determined by the desired productivity of the conversion unit, the activity of the particulate catalyst and, in the case of immobilized microbial cell catalyst, the concentration of cells in the particulate catalyst. The bed should be deep enough to supply sufficient enzyme activity for the desired productivity of the unit and not so deep as to prevent the desired flow discussed hereinafter. At times it may be advisable to admix the catalyst with a particulate material such as diatomaceous earth, perlite or powdered cellulose added in the amount of up to about 80 volume percent of the bed to give the bed a more porous structure. Beds about 1 to 6 cm deep normally meet the desired productivity and flow requirements. Particularly suitable units for preparing such beds include standard filtration equipment such as a horizontal pressure leaf filter or a plate-and-frame filter press.

The conversion is run under controlled temperature as well as pH conditions to maximize productivity while minimizing substrate, product and catalyst degradation. The temperature is limited to between about 15° to 45° C and preferably between about 35° and 40° C. The activity of the catalyst drops off considerably at temperatures much below 15° C while temperatures much above 45° C result in considerable decomposition of the penicillin and 6-APA and appreciable denaturization of the catalyst. As indicated hereinbefore, pH control is critical to high conversion of penicillin to 6-APA, and the pH of the process is therefore limited to from about 6.5 to 9.0. A pH much below 6.5 results in considerably reduced enzyme activity and in enhanced penicillin degradation, while a pH much greater than 9.0 accelerates not only penicillin degradation but also enzyme denaturization. The pH is preferably maintained between about 7.5 and 8.2 when the catalyst is derived from *Proteus rettgeri*.

In practice, the bulk of the process stream is maintained at the desired temperature and pH in a stirred tank or reservoir. A small portion of the stream is continuously passed through the catalyst bed and quickly returned to the reservoir where the acid formed during the passage through the bed is neutralized by a suitable base such as sodium hydroxide to maintain the pH within the desired range. Such a system can be adapted to batch, semi-continuous or continuous operation.

The flow rate of the process stream through the catalyst bed is also of critical importance in assuring optimum conversion of penicillins to 6-APA, and should be at least 0.4 bed volume per minute. Flow rates much below this value not only cause a considerable reduction of catalyst utilization resulting from poorer diffusion of the substrate and product within the catalyst bed but also enhance the degradation of substrate, product and catalyst from the increase localized acidity present in the bed.

The recycling of the process stream through the catalyst bed is continued until the penicillin in the stream has been substantially (at least 80 percent) converted. The 6-APA in the stream may then be either isolated or reacted to a desired penicillin by conventional means.

The following examples merely illustrate the process of the present invention and are not to be construed as limiting the invention, the scope of which is defined by the appended claims.

EXAMPLE 1

A *Proteus rettgeri* [ATCC 31052 (ATCC 9250); Pfizer Culture 18470-76-60] fermentation broth, grown under submerged aerobic conditions at 28° C and pH 6.8–7.0 on lactic casein substrate, was centrifuged and the separated cells were washed with water. A suspension of 317 kg of the washed cells in 2120 liters of water was treated with 16.3 kg of 25 weight percent aqueous glutaraldehyde and stirred for 17 minutes at 21° C. To the treated suspension under nitrogen was added 162.6 kg glycidyl methacrylate and the suspension was stirred for 2 hours at 22° C. Then 30.4 kg N,N'-methylenebisacrylamide, 27.6 kg dimethylaminopropionitrile and 3.3 kg ammonium persulfate were added and the mixture, at pH 7.1, was stirred for 2 hours at 25°–33° C. The reaction slurry was filtered and washed with water to give a wet particulate deacylation catalyst containing 918 units penicillin acylase per gram of dry catalyst.

A mixture of the wet catalyst (5.1 kg dry) and diatomaceous earth filter aid (7.1 kg) was diluted with water to give a slurry with a solids content of about 160 g/liter. A horizontal leaf pressure filter containing eight leaves 18 inches (46 cm) in diameter was pressurized with water to a gauge pressure of 40 psi (2.7 atm). The catalyst slurry was then charged to the filter at the rate of about 20 liters/min, the filtrate being recycled to the slurry tank until essentially clear. The resulting catalyst bed was uniformly loaded on the filter leaves, with a depth of 2.3 cm on the top leaf and 2.8 cm on each of the remaining seven leaves. The bed volume was about 37 liters with a total activity loading of $4.32 \times 10^6$ units.

An aqueous solution of potassium penicillin G was prepared by dissolving 3.0 kg of the penicillin (purity 97.1 percent) in sufficient water in an agitated holding tank to give a final volume of 130 liters. The solution was then recirculated through the catalyst bed and back into the holding tank, the reaction solution in the tank being maintained at a temperature of 37°–39° C by use of an external heat exchanger in the return line and at a pH of 7.8–8.1 by the incremental addition of 1N sodium hydroxide. The recycling was continued until the penicillin was greater than 90 percent converted to 6-APA as determined by the amount of NaOH added. The system was then drained and rinsed with about 12 liters of water, a fresh penicillin solution was prepared and the recycling was resumed. A sample of the combined product stream and system rinse was extracted twice at ph 2.3 and 10° C with 0.25 volume of ethyl acetate and the extracted sample was assayed for 6-APA.

Table I summarizes the results from the operation of the system through several consecutive cycles:

TABLE I

| Cycle[1] | 1 | 3 | 4 | 5 | 6 |
|---|---|---|---|---|---|
| Charge, kg K pen G | 3.0 | 3.0 | 3.0 | 3.0 | 2.0 |
| Pressure drop thru bed psi (atm) | | | | | |
| Start | 42 (2.9) | 44 (3.0) | 42 (2.9) | 41 (2.8) | 41.5 (2.8) |
| Finish | 43 (2.9) | 44 (3.0) | 41.5 (2.8) | 41 (2.8) | 41.5 (2.8) |
| Recirculation rate, liters/min | | | | | |
| Start | 66 | 50 | 50 | 50 | 50 |
| Finish | 58 | 50 | 50 | 48 | 48 |
| Reaction time, hr/mole | 0.83 | 0.86 | 1.01 | 1.03 | 1.20 |
| Conversion, % | 93 | 96 | 96 | 93 | 96 |
| Yield 6-APA, %[2] | 94 | 82 | 89 | 94 | 86 |

[1] Cycle 2 aborted by electrical failure; results not significant
[2] Stoichiometric yield based on converted penicillin The solvent-extracted product stream can be concentrated at 40° C and pH 7, and the 6-APA content of the concentrate either crystallized at pH 3.6 or acylated to a desired penicillin.

The above system can suitably be operated at pH 9.0 and 45° C, or at pH 6.5 and 15° C, using a catalyst bed depth of from 1 to 6 cm with a recirculation flow rate through the bed of 0.4 bed volume/min or greater.

EXAMPLE 2

Wet particulate immobilized *Proteus rettgeri* cells (5.1 kg dry) prepared as in Example 1 and containing 690 units penicillin acylase per gram of dry catalyst was combined with 5.1 kg diatomaceous earth filter aid in sufficient water to give a slurry with a solids content of about 90 g/liter.

A plate-and-frame filter press having 16 frames each with a chamber depth of 1.0 inch (2.54 cm) and a chamber area of 112 in$^2$ (723 cm$^2$) for a total chamber volume of 1.04 ft$^3$ (29.4 liters) was pressurized with water to a gauge pressure of 20–25 psi (1.4–1.7 atm). The catalyst slurry was then introduced to the filter at a constant flow rate until the bed was fully formed, the pressure drop through the filter being increased to 40 psi (2.7 atm) and the filtrate recycled until clear. This resulted in a uniform chamber loading with each of the chambers 85 to 90 percent full. The total activity loading was 3.5 × 10$^6$ units.

Aqueous penicillin solutions were prepared and the recycle system was operated as in Example 1 using potassium penicillin G (purity 96.7 percent), a solution volume of 50 liters, an operating temperature of 37°–39° C and pH of 7.8–8.0, and a system rinse of 20 liters. Table II summarizes the results from the operation of this unit:

TABLE II

| Cycle | 1 | 2 | 3$^{(1)}$ | 4 |
|---|---|---|---|---|
| Charge, kg K pen G | 2.0 | 3.0 | 2.0 | 3.0 |
| Pressure drop thru bed, psi (atm) | | | | |
| Start | 18 (1.2) | 30 (2.0) | 58 (3.9) | 32 (2.2) |
| Finish | 26 (1.8) | 46 (3.1) | 66 (4.5) | 45 (3.1) |
| Recirculation rate, liters/min | | | | |
| Start | 25 | 26 | 22 | 25 |
| Finish | 24 | 23 | 20 | 24 |
| Reaction time | | | | |
| hr/mole | 0.77 | 0.78 | 0.97 | 0.87 |
| Conversion, % | 95 | 95 | 96 | 93 |
| Yield 6-APA, % | 93 | 89 | 94 | 90$^{(2)}$ |

$^{(1)}$Catalyst bed discharged from filter following Cycle 3, reslurried in water and recharged to filter for Cycle 4
$^{(2)}$Yield isolated 6-APA 91%

Penicillin acylase-containing *Escherichia coli* ATCC 9637 cells may conveniently replace the *Proteus rettgeri* cells in this conversion.

Penicillin acylase isolated from penicillin acylase-producing microbial cells, such as *Proteus rettgeri* ATCC 31052 and *Escherichia coli* ATCC 9637, and immobilzed as in U.S. Pat. No. 3,925,157 to give a particulate deacylation catalyst of equivalent activity may also be substituted for the immobilized microbial cell catalyst in this procedure.

What is claimed is:

1. In the process for the enzymatic conversion of a penicillin to 6-aminopenicillanic acid wherein an aqueous solution of said penicillin is contacted with a particulate immobilized penicillin acylase catalyst, the improvement which comprises recirculating said solution through a bed comprising said particulate catalyst at a flow rate of at least 0.4 bed volume per minute while maintaining said solution at a temperature of from about 15° and a pH of from about 6.5 to 9.0 and continuing said recirculation until said penicillin is substantially converted to said acid, said bed having a depth of up to about 6 centimeters.

2. The process of claim 1 wherein said penicillin is potassiun penicillin G.

3. The process of claim 1 wherein said bed has a depth of from about 2 to 3 centimeters.

4. The process of claim 1 wherein said particulate catalyst comprises immobilized *Proteus rettgeri* cells containing said enzyme.

5. The process of claim 1 wherein said temperature is from about 35° to 40° C and said pH is from about 7.5 to 8.2.

* * * * *

UNITED STATES PATENT AND TRADEMARK OFFICE
CERTIFICATE OF CORRECTION

PATENT NO. : 4,113,566
DATED : September 12, 1978
INVENTOR(S) : James J. Hamsher et al It is certified that error appears in the above-identified patent and that said Letters Patent are hereby corrected as shown below:

Column 2 line 35 change "general" to --genera--.

Column 2 line 48 insert a comma after "acrylate".

Column 4 line 39 change "ph" to --pH--.

Column 5 in TABLE II, first column headed "Cycle", last line insert a comma after "Reaction time".

Column 6, claim 1 line 9, after "15°" insert --to 45°C--.

Signed and Sealed this

Twenty-seventh Day of February 1979

[SEAL]

Attest:

RUTH C. MASON
Attesting Officer

DONALD W. BANNER
Commissioner of Patents and Trademarks